United States Patent
Lin (10) Patent No.: US 12,171,252 B2
(45) Date of Patent: Dec. 24, 2024

(54) FREEZE-DRIED PROBIOTIC FOODSTUFFS

(71) Applicant: IMAGILIN TECHNOLOGY, LLC, Frederick, MD (US)

(72) Inventor: Jhy-Jhu Lin, Frederick, MD (US)

(73) Assignee: IMAGILIN TECHNOLOGY, LLC, Frederick, MD (US)

( * ) Notice: Subject to any disclaimer, the term of this patent is extended or adjusted under 35 U.S.C. 154(b) by 0 days.

(21) Appl. No.: 16/356,692

(22) Filed: Mar. 18, 2019

(65) Prior Publication Data
US 2019/0282498 A1 Sep. 19, 2019

Related U.S. Application Data

(60) Provisional application No. 62/761,335, filed on Mar. 19, 2018.

(51) Int. Cl.
| | | |
|---|---|---|
| A23L 33/135 | (2016.01) | |
| A23B 4/037 | (2006.01) | |
| A23B 4/22 | (2006.01) | |
| A23B 7/024 | (2006.01) | |
| A23B 7/155 | (2006.01) | |
| A23C 9/123 | (2006.01) | |
| A23L 3/3571 | (2006.01) | |
| A23L 3/44 | (2006.01) | |
| A61K 9/00 | (2006.01) | |
| A61K 35/744 | (2015.01) | |
| A61K 35/747 | (2015.01) | |

(52) U.S. Cl.
CPC .......... *A23L 33/135* (2016.08); *A23B 4/037* (2013.01); *A23B 4/22* (2013.01); *A23B 7/024* (2013.01); *A23B 7/155* (2013.01); *A23C 9/1234* (2013.01); *A23L 3/3571* (2013.01); *A23L 3/44* (2013.01); *A61K 9/0056* (2013.01); *A61K 35/744* (2013.01); *A61K 35/747* (2013.01); *A23V 2002/00* (2013.01); *A23V 2400/143* (2023.08); *A23V 2400/413* (2023.08)

(58) Field of Classification Search
CPC ............. A61K 9/0056; A61K 35/747; A61K 35/744; A23L 33/135; A23L 3/44; A23L 3/3571; A23L 19/00; A23B 4/037; A23B 7/024; A23B 7/155; A23B 4/22; A23C 9/1234; A23C 9/133; A23C 9/1236; A23Y 2280/15; A23Y 2220/35; A23V 2002/00; A61P 1/14

See application file for complete search history.

(56) References Cited

U.S. PATENT DOCUMENTS

| | | | | |
|---|---|---|---|---|
| 5,968,569 | A | 10/1999 | Cavadini et al. | 426/61 |
| 9,289,008 | B1 * | 3/2016 | Lin | A23L 33/135 |
| 9,986,750 | B2 * | 6/2018 | Carpenter | A23K 10/18 |
| 10,195,237 | B2 * | 2/2019 | Lin | A61K 38/50 |
| 10,946,050 | B2 * | 3/2021 | Lin | A61K 35/744 |
| 11,633,437 | B2 * | 4/2023 | Lin | A61K 31/555 424/93.45 |
| 2003/0147938 | A1 * | 8/2003 | Hirsch | A23L 33/20 424/439 |
| 2008/0102163 | A1 * | 5/2008 | O'Toole | A21D 13/20 426/61 |
| 2009/0110773 | A1 * | 4/2009 | Dwivedi | A23L 33/135 426/61 |
| 2010/0009034 | A1 * | 1/2010 | Ling | C12N 1/205 426/43 |
| 2010/0098806 | A1 * | 4/2010 | Van Drunen | A23B 7/16 426/61 |
| 2011/0104327 | A1 | 5/2011 | Kirejevas | 426/2 |
| 2013/0029012 | A1 | 1/2013 | Girard | 426/103 |
| 2014/0335227 | A1 * | 11/2014 | Hollard | A23L 29/065 435/253.4 |
| 2015/0246082 | A1 * | 9/2015 | Lin | A61K 36/81 424/93.45 |
| 2016/0346337 | A1 * | 12/2016 | Garner | A23K 50/20 |
| 2017/0020929 | A1 * | 1/2017 | Lin | A61K 31/704 |

FOREIGN PATENT DOCUMENTS

| | | | | |
|---|---|---|---|---|
| WO | WO-02076471 A1 * | 10/2002 | | A23K 10/18 |
| WO | WO-2015186998 A1 * | 12/2015 | | A23L 33/00 |

OTHER PUBLICATIONS

Bhat, AR et al. Bacillus subtilis natto: a non-toxic source of poly-y-glutamic acid that could be used as a cryoprotectant for probiotic bacteria. AMB Express. 2013. 3:36. 9 pages. (Year: 2013).*

Notification of Transmittal of the International Search Report and the Written Opinion of the International Searching Authority, or the Declaration dated Jun. 20, 2019, issued by the U.S. Patent Office in corresponding application PCT/US2019/022952.

* cited by examiner

*Primary Examiner* — David W Berke-Schlessel
*Assistant Examiner* — Susan E. Fernandez
(74) *Attorney, Agent, or Firm* — Nevrivy Patent Law Group P.L.L.C.

(57) ABSTRACT

Compositions wherein foodstuffs act as carriers of freeze-dried probiotics provide new means for administration of probiotics. The products that are easily shipped may be eaten as purchased or mixed with other ingredients to provide variety in the diet while administering beneficial probiotic organisms to the gastrointestinal tract.

8 Claims, 2 Drawing Sheets

FREEZE-DRIED PROBIOTIC FOODSTUFFS

DETAILS OF RELATED APPLICATIONS

This application claims the benefit under 35 U.S.C. § 119(e) of U.S. Provisional Application No. 62/761,335 filed on Mar. 19, 2018 and titled "Novel dried probiotic foods can be stored at room temperature and elevated temperatures"; which is fully incorporated herein by reference.

FIELD OF THE INVENTION

This invention is in the field of food technology, most particularly in the field of probiotic products, their production and use. Prior patents teaching and claiming related subject matter are U.S. Pat. No. 9,289,008 B1 that teaches and claims *P. acidilactici* NRRL B-50517 and U.S. Pat. No. 10,195,237 that teaches compositions and methods for treating inflammatory-related diseases or conditions using *P. acidilactici* probiotics are incorporated herein by reference as though copied herein.

BACKGROUND OF THE INVENTION

Probiotics are live microorganisms which, when administered in adequate amounts, confer health benefits on the host. Many probiotics-related health benefits have been reported such as decreases in symptoms from antibiotics-induced diarrhea, acute diarrhea, traveler diarrhea, allergy, respiratory and urinary tract infections, inflammatory bowel disease, irritable bowel syndrome, colon and bladder cancer, rheumatoid arthritis, obesity and type-2 diabetes. Foods that provide targeted health benefits are particularly popular. Foods that provide probiotic microorganisms in a suitable matrix and in sufficient concentration are of particular interest. Currently, dairy products are the main group of foodstuffs used to deliver probiotic bacteria. Some current laws establish minimum viable quantities of $10^6$-$10^7$ CFU/g or CFU/mL such as those issued by the International Dairy Federation (IDF). Although dairy products are still the favored products used to incorporate probiotic bacteria, there is a disadvantage. Because of their high lactose and cholesterol content refrigeration is required. Furthermore, with many consumers now preferring vegetarian diets, the demand for vegetarian-based probiotic-containing products exists and will undoubtedly increase. Finally, there is always a desire for products having new flavors and textures.

Food processing may involve many and varied procedures. It is essential, in the practice of the invention, that processes used in preparation of the final products not negatively affect the activity of the probiotic. Hence, the processes of blending, pumping, pasteurization and freezing must be managed with care to avoid undue decrease in the viability of the probiotic bacteria. More importantly, probiotic products must be stable when stored at room temperature and, at times, at higher temperatures for transportation, storage and handling. This is especially important when working with non-spore-forming probiotics, which are preferred from regulatory and safety perspectives.

SUMMARY OF THE INVENTION

The object of this invention is to provide freeze-dried probiotic food products for delivery of probiotic organisms and means of making such products. The products of the invention provide many advantages over the presently available probiotic food products since the final products can often be stored for long periods of time without refrigeration. Because many of the freeze-dried probiotic products are sold in dried form they can be shipped and stored readily. This makes their use as snacks and ingredients for use in food preparation more economical and convenient. Products of invention include foods wherein the probiotics are incorporated into or adherent to the food product. While the invention includes any food product that can be used as a "carrier" for the probiotics, of particular interest are freeze-dried food products such as freeze-dried fruits, vegetables and nuts or dried meats such as, for example, freeze-dried beef.

The production of the compositions of the invention requires preparation of the carriers, whether meat, fruit, nuts, or other materials to which the probiotics are applied or added. Since most probiotics are temperature sensitive, the temperature during and after the time the probiotics are applied to or incorporated in the final products must be controlled. The food to which the probiotics are to be added must be cleaned and sanitized in accord with regulations which apply to food products.

The probiotics foods are prepared by freeze drying. The freeze drying process renders the probiotics essentially inactive until after ingestion. Although the genus *Lactobacillus* can be applied onto freeze-dried probiotic foods, preferred organisms for use in the practice of the invention are of the genus *Pediococcus*. A particularly preferred strain is *Pediococcus acidilactici* NRRL B-50517. Food products of the invention may be provided as snacks, such as dried fruits, vegetables or nuts or the products sold may be added during preparation of more complex mixtures such as salads and desserts. Dried products that are easily packaged and shipped are particularly desirable.

DETAILED DESCRIPTION

This invention may be practiced using any probiotic organism that will be viable after ingestion to provide desired benefits associated with administration of probiotic organisms. The selection of organisms to be used in the practice of the invention is within the skill of those knowledgeable in preparation and use of probiotics. Food products used in practice of the invention includes fruit, vegetables, dairy products and other food products. The only stipulation is that the foods can withstand the freeze drying processes. Foods which may be used for treatment with the probiotics include foods that have been treated with antioxidants, salts, sugars, preservative and carriers used in the food industry. The foods to be treated with probiotics may have undergone heat treatment, exposure to cold (such as frozen foods) or freeze-drying. Foods such as mixed snacks may also be used in the methods of the invention to undergo processes for applying probiotics.

The probiotic compositions used in the processes of the invention include, but are not limited to, probiotic solutions, which may be mixtures of freeze-dried probiotics dissolved in water, sugar solutions, salt solutions or any other liquid that will not adversely affect the activity of the probiotics upon reaching the digestive tract. Similarly, probiotics in fermented cultures such as those grown in the MRS broth, harvested probiotic cultures and cultures blended with water, sugar or salt solutions may be used. The probiotic cultures may also be prepared by fermentation in dairy products such as milks, including soy milks. The freeze-dried probiotics can also be used in powders. Using methods of the invention it is possible to amplify the probiotic content up to $10^6$ cfu/g. While the *Pediococcus* and *Lactobacillis* organisms have been suggested and exemplified, other organisms may be used in the methods of the invention.

Methods used in applying probiotics to the foods before freeze drying include but are not limited to, dipping the food in solutions containing the probiotics, spraying probiotic/containing solutions on the foods and dusting the food with dried powders. In many instances it is most desirable that the food products be stable at room temperature.

In a preferred method of the invention pieces of freeze-dried foodstuff are coated with a layer of freeze-dried probiotic bacteria in a manner that results in the bacteria adhering to the pieces of foodstuffs. In some examples the bacteria of the genus *Pediococcus* were used. The bacteria of the species *acidilactici* (e.g. *Pediococcus acidilactici* NRRL B-50517) were exemplified in the examples. However, incorporation by mixing freeze-dried probiotics into the food product is also appropriate.

It may also be beneficial to have a preservative in the coating layer. Antioxidants such as Vitamin C may be added to the products during processing.

Fruits such as strawberries, blueberries and raspberries may be used in accord with the methods disclosed herein and may be used whole in preparation of the final products. Larger fruits such as mangoes, bananas, apples and pears may be cut into small pieces. All of the fruit products may, but need not, be dried before coating with the probiotics. Vegetables such as sweet potatoes, potatoes and plantains will usually be cut into smaller pieces for processing, while smaller vegetables such as peas and beans may be processed whole for use in the methods of the invention.

Materials and Methods:

For purposes of this specification and the accompanying claims, the term "meats" includes beef, poultry (e.g. chicken, turkey, goose, duck), pork and fish as well as edible organs from any of species used for meat. For purposes of this specification and the accompanying claims, the term "dairy products" includes, but is not limited to, yogurt and soft cheeses such as labneh, pot cheese, farmer's cheese and cottage cheese.

The practice of the invention requires several steps. Materials such as fruits and vegetables are cleaned by means usual in the food arts before exposure to the probiotics. Additional steps such as drying (including freeze drying) may be used in processing the foodstuffs for use in the final products. Meat products may be cooked or salted (such as brined) and dried in accord with the usual methods used for preparation of food for human consumption in order to destroy disease-causing organisms. Methods and materials used in the examples may be replaced in other settings using materials and methods which are functionally the same and/or result in similar outcomes. Availability of equipment will determine use in methods of the invention as long as equivalent results are obtained. Use of methods for larger scale production would produce equivalent results. Most preferred are final products that are easily shipped and stored. However, the methods may be applied to more perishable products such as dairy products with good effect.

Meat pre-treatment: Beef meat or chicken livers were rinsed with large amounts of water, dried with paper towels, cut into ⅛ inch to 2 inch cubes, heat seared in olive oil. Seared cubes were removed and placed on paper towels and cooled to room temperature. Cooled cubes were treated with probiotic powder or probiotic solution as detailed below, and mixed homogenously and then placed trays for freeze-drying.

Alternatively, the meats may be treated with salt, freeze dried or subjected to antioxidant treatment to destroy harmful organisms, Coating with probiotic powder (hereinafter 5051 powder): Pieces of foodstuff (e.g. seared and cooled cubes as described above) were placed into containers with probiotic powder (40 g to 80 g *P. acidilactici* NRRL B-50517 powders, 10 billion CFU/g for 200 g to 1 kg of foodstuff). The pieces were rolled in probiotic-containing powder in order to coat the pieces, then transferred to trays for freeze-drying. In some instances the trays were covered with parchment paper.

Coating with probiotic solution (hereinafter 5051 solution): Pieces of foodstuff (e.g. seared and cooled cubes as described above) were placed into containers with a *Pediococcus acidilactici* NRRL B-50517 solution [mixed 20 g of *Pediococcus* fermentative probiotics of freeze-dried powders (catalogue number PA-5051FD, Imagilin Technology, LLC) with 80 ml water]. The pieces were mixed in the solution for 45 secs to one minute then transferred to trays for freeze-drying. Sometimes the trays were covered with parchment paper. Alternatively, pieces of food may be coated with probiotic fermentative culture or yogurt containing the probiotics.

Calculation of CFU: in some examples of the invention 0.2 g to 0.4 g probiotic bacteria coated foodstuff was transferred into 5 ml saline solution, and mixed well. A series of dilutions was prepared and plated in 100 ul aliquots onto MRS plates and incubated overnight. Colonies were then counted. The CFU determination was made before and after freeze-drying and/or at other steps in the process.

Figure 1:
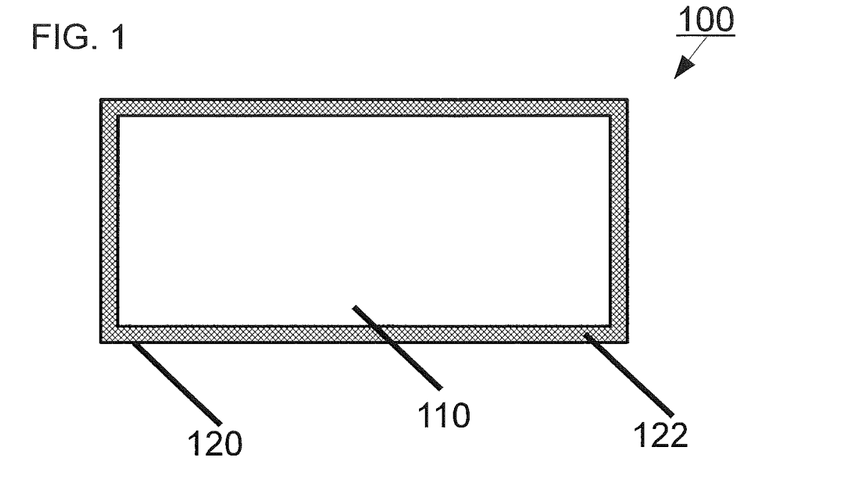
FIG. 1 is a schematic representation of a transverse cross section of preparation of a probiotic freeze-dried food.
Figure 2:
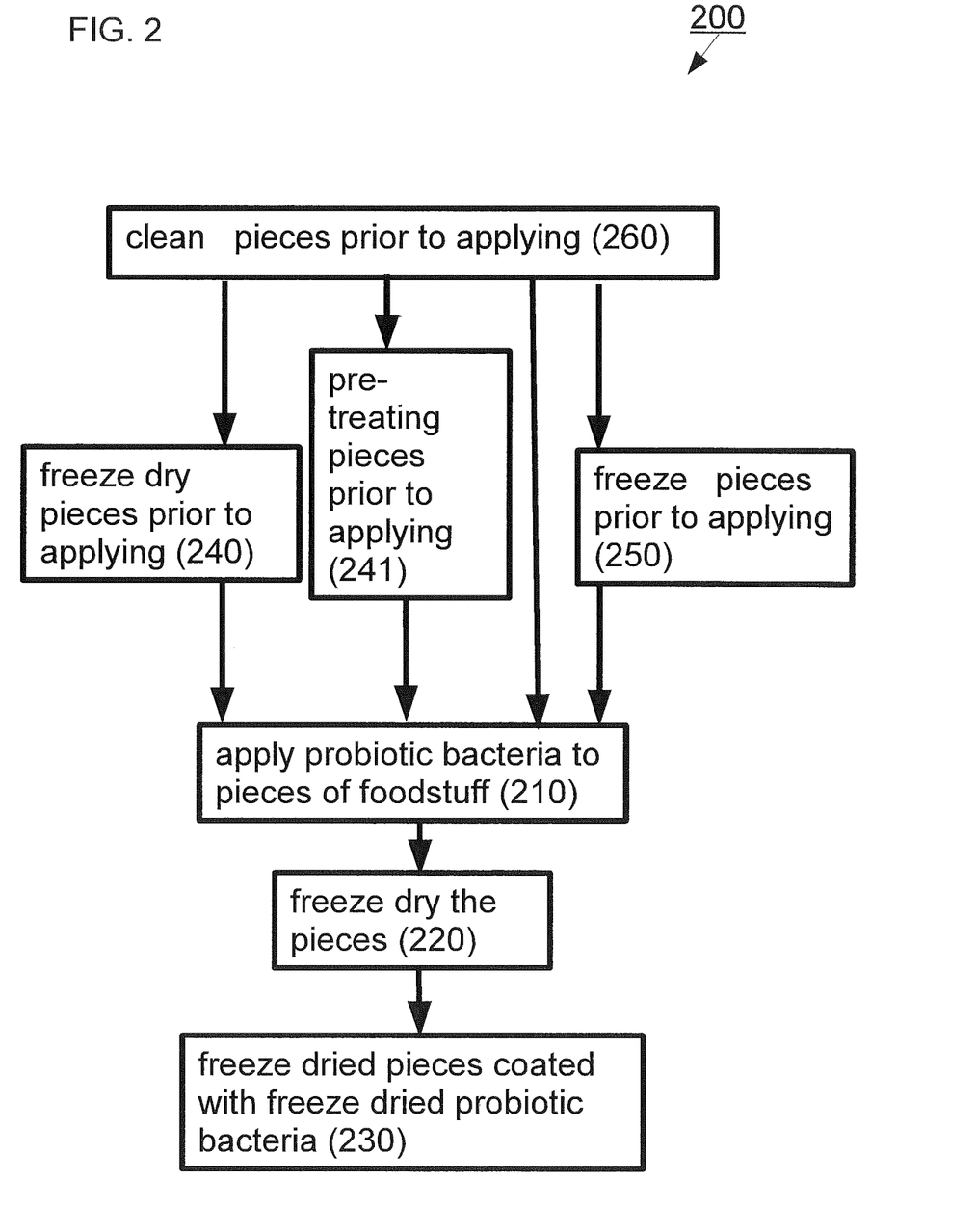
FIG. 2 is a flow diagram of several steps that may be used in practice of the invention.

Referring with particularity to processes of the invention that may be used to prepare the foodstuffs for application of freeze dried probiotics to the foodstuffs, food stuffs enter into the process of preparation, and the cleaning process may be initiated using non-heat treatment or heat treatment. Foodstuffs which have been subjected to non-heat treatment may then be frozen, or may not be frozen. In another stream, foodstuffs upon entering the heat treatment stream may later be non-frozen or frozen. At the end, all foodstuffs from the preparatory process are then passed on to the process for addition of the probiotic-containing materials. The probiotics may be applied as yogurt probiotic compositions, as fermented growth probiotic compositions, as probiotic-containing solutions or as probiotic powder compositions. All products from the latter four probiotic application streams now pass through the freeze-drying process, producing freeze-dried probiotic products.

Additional embodiments of processes of the present invention can be described as follows. The foodstuffs are cleaned, then may be heat treated or may undergo treatment that does not involve heating. The products of the heat treatment stream may then be frozen, but need not be frozen. Similarly, products of the stream that does not involve heating may pass on in the production process after being frozen or without being frozen. The stream of prepared foodstuffs products then may pass on to the process for application or incorporation of the freeze dried probiotic. The application or incorporation of probiotics may be in the form of yogurt prepared products, fermented growth probiotics, probiotic solutions or probiotic powders. All of the products from yogurt, fermented growth probiotic, probiotic solution or probiotic powder streams, regardless of means of application of the probiotics, then undergo freeze drying to provide probiotic freeze-dried final products.

EXAMPLE 1

Detection of Live Probiotics from *Pediococcus* Freeze-Dried Beef Meat and Chicken Livers Heat-seared beef and/or chicken livers were prepared for coating with probiotic bacteria. Beef meat or chicken livers were subjected to "meat pre-treatment" as described above, then coated with either 5051 powder or 5051 solution (see above) and freeze dried. CFU/g were determined after freeze-drying. Results are summarized in table 1.

TABLE 1 recovery of viable bacteria from cooked meat products after freeze-drying

| Substrate | NRRL B-50517 | CFU/g |
|---|---|---|
| Beef meat | 5051 powders | $9.03 \times 10^8$ |
|  | 5051 solutions | $2.24 \times 10^8$ |
| Chicken Livers | 5051 powders | $1.68 \times 10^9$ |
|  | 5051 solutions | $1.18 \times 10^8$ |

Results presented in table 1 indicate that bacteria remained viable after freeze-drying on heat-treated beef and/or chicken livers.

EXAMPLE 2

Applications of *Lactobacillus fermentum* and *Pediococcus acidilactici* NRRL B-50517

In order to determine whether freeze-drying can be applied to bacteria from strains other than *Pediococcus acidilactici* NRRL B-50517 a similar preparation method using probiotic *Lactobacillus fermentum* was used. Both live *Lactobacillus fermentum* and *P. acidilactici* were detected from *Lactobacillus* freeze-dried sliced apples and *Pediococcus* freeze-dried apples at room temperature or those treated at 65° C. for 10 minutes. Survival of *P. acidilactici* NRRL B-50517 through freeze-drying process is 540 times better than *Lactobacillus fermentum*, and 2,850 times better once the probiotic freeze-dried products were treated by elevated temperature at 65° C. for 10 minutes (table 2). These results demonstrated the similar preparation methods are applicable using different probiotic bacteria. However, the survival rates of *Lactobacillus fermentum* is much less (about 1,000 folds less) than those of *P. acidilactici* NRRL B-50517

Results are summarized in table 2.

TABLE 2

Detection of live probiotics either from *Lactobacillus* probiotic freeze-dried apples* or from *Pediococcus* probiotic freeze-dried apples**

| Treatment of probiotic freeze-dried apples | Numbers of *Lactobacillus fermentum* (CFU/g) from probiotic freeze-dried Gala apples[1] | Numbers of *Pediococcus acidilactici* NRRL B-50517 (CFU/g) from probiotic freeze-dried Gala apples[1] |
|---|---|---|
| Room temperature | $4.25 \times 10^5$ | $2.30 \times 10^8$ |
| 65° C. 10 minutes | $1.00 \times 10^5$ | $2.85 \times 10^8$ |

*Apples were cut into ¼ inch slices, then those pieces were cut into halves. Apple slices were transferred into the *Lactobacillus fermentum* solution [mixed 20 g of *Lactobacillus* fermentative probiotics for freeze-dried powders 10 billion CFU/g, with 80 ml water], then mixed with the probiotic solution for 45 secs to a minute and then transferred *Lactobacillus* coated apple on the freeze-drying trays covered with parchment paper and freeze dried.
**Cut apples into ¼ inch slices, then cut those into halves. Transferred apple slices into the *Pediococcus acidilactici* NRRL B-50517 solution [mixed 20 g of *Pediococcus* fermentative probiotics for freeze-dried powders 10 billion CFU/g with 80 ml water], mixed the sliced apples and probiotic solution for 45 secs to a min, transferred *Pediococcus* coated apple on the freeze-drying trays covered with parchment paper and freeze dried.
[1]Measured 0.2 g to 0.4 g of *Lactobacillus* probiotic freeze-dried sliced apples or *Pediococcus* probiotic freeze-dried sliced apples, transferred the sliced apple into 5 ml saline solution, and mixed well. Performed series of dilutions, and plated 100 ul of desirable diluted solution onto MRS plates and incubated overnight, then counted the colonies.

EXAMPLE 3

Increasing Loading of Bacteria in Coating

In order to examine the possibility of increasing the amount of CFUs per gram in freeze-dried apples, we increased the loading amount prior to freeze-drying.

This is important because when one takes higher amounts of live probiotics, the beneficial effects are observed more quickly, especially for those suffering from digestive disorders. Appling of higher amounts of *P. acidilactici* NRRL B-50517 onto the products prepared by the freeze-dried process resulted in proportionally higher amounts of live *Pediococcus* detected. These results demonstrate the possibility of making probiotic freeze-dried products with any desired amount of live bacteria depending on the concentrations applied before freeze-drying. Results are summarized in table 3.

TABLE 3

Detection of live probiotics from *Pediococcus* freeze-dried apples using different amounts of *P. acidilactici* NRRL B-50517

| Amounts of *P. acidilactici* NRRL B-50517 (CFU) per kg of Fuji apples (fresh weight)* | Numbers of *P. acidilactici* NRRL B-50517 (CFU/g)** from probiotic freeze-dried Gala apples |
|---|---|
| $4 \times 10^{12}$ | $4.85 \times 10^9$ |
| $4 \times 10^{11}$ | $6.85 \times 10^8$ |
| $4 \times 10^{10}$ | $6.38 \times 10^7$ |

*Cut apples into ¼ inch thick slices, then cut those into halves, then transferred apple slices into the *Pediococcus acidilactici* NRRL B-50517 solution [mixed 20 g of different concentration of *Pediococcus* fermentative probiotics for freeze-dried powders with 80 ml water], mixed the sliced apples and probiotic solution for 45 secs to a min, transferred *Pediococcus* coated apple on the freeze-drying trays covered with parchment paper and freeze dried.
**Measured 0.2 g to 0.4 g of *Pediococcus* probiotic freeze-dried apples, transferred the slice apple into 5 ml saline solution, and mixed well. Performed series of dilution, and plated 100 ul of desirable diluted solution onto MRS plates and incubated overnight and then counted the colonies.

EXAMPLE 4

Pretreatment of Apples Has No Apparent Effect on Probiotic Viability of Probiotic Freeze-Dried Food In order to determine the effects of boiling and/or freezing foodstuffs on the ability to make probiotic coated freeze-dried foodstuffs an experiment was conducted in apples. Results summarized in table 4 indicate that *P. acidilactici* NRRL B-50517 is able to survive freeze-drying when applied as a coating to frozen apples, heat treated apples, and heat treated and frozen apples. More important, similar viabilities of probiotics were obtained from frozen apples, heat-treated apples, and heat-treated and frozen apples. This indicates that *P. acidilactici* NRRL B-50517 can survive the freeze-drying process from on foodstuffs subjected to various pre-treatments.

TABLE 4

Detection of live probiotics from *Pediococcus* freeze-dried apples using different pretreatment of apples followed by treating with probiotic solutions

| Pretreatment of apples* | Numbers of *P. acidilactici* NRRL B-50517 (CFU/g) ** |
|---|---|
| Boiled apples[1] | $2.60 \times 10^7$ |
| Frozen apples[2] | $3.40 \times 10^7$ |
| Boiled, frozen apples[3] | $8.93 \times 10^7$ |

*[1]Boiled apples-transferred the sliced apples to the 90 C. heated saline solutions for 30 seconds to 1 minute, took apple slices out and cooled to room temperature, then coated with probiotic solution 5051 as described hereinabove. [2]Frozen apples-transferred the sliced apples to 10% sucrose solution, mixed uniformly, transferred to −20° C. freezer to freeze the apples overnight to a week, took frozen apple slices then coated with probiotic solution 5051 as described hereinabove. [3]Boiled then frozen apples-transferred the sliced apples to the 90° C. heated saline solutions for 30 seconds to 1 minute, took apple slices out and cooled to room temperature, transferred the sliced apples to 10% sucrose solution, mixed uniformly, transferred to −20° C. freezer to freeze the apples overnight to a week, took boiled, frozen apple slices then coated with probiotic solution 5051 as described hereinabove.

*Measured 0.2 g to 0.4 g of *Pediococcus* probiotic freeze-dried apples, transferred the sliced apple into 5 ml saline solution, and mixed well. Performed series of dilution, and plated 100 ul of desirable diluted solution onto MRS plates and incubated at the incubator overnight to count the colonies.

EXAMPLE 5

Powder vs. Solution as Coating Agent

In order to determine whether there is a significant difference between coating with powder or solution, we conducted a direct comparison using multiple foodstuffs as substrates. One of the motivations for this experiment is that some industrial manufacturing process may prefer spraying or coating the powders onto the products directly. In this experiment either *Pediococcus* solution or Probiotic powder was applied directly onto blueberry, sliced strawberry, sliced green bean and sliced sweet potato followed by the freeze-drying to see the survival of *P. acidilactici* NRRL B-50517. CFU were then determined from the freeze-dried products.

Results are summarized in table 5. Results indicate that high amounts of viable *Pediococcus* bacteria were present in freeze-dried products prepared using *Pediococcus* probiotic powders directly.

TABLE 5

Detection of live probiotics from *Pediococcus* freeze-dried fruits or vegetables using probiotic powders or probiotic solution *

| substrate | Type of *P. acidilactici* NRRL B-50517** | Numbers of *P. acidilactici* NRRL B-50517 (CFU/g) ** from probiotic freeze-dried products | Water Activity |
|---|---|---|---|
| Blueberry | Powders[1] | $4.90 \times 10^8$ | 0.32 |
| | Solution[2] | $6.25 \times 10^7$ | 0.34 |
| Strawberry | Powders[1] | $7.90 \times 10^8$ | 0.25 |
| | Solution[2] | $1.00 \times 10^8$ | 0.18 |
| Green Bean | Powders[1] | $6.00 \times 10^8$ | 0.31 |
| | Solution[2] | $1.25 \times 10^8$ | 0.20 |
| Sweet potato | Powders[1] | $4.00 \times 10^8$ | 0.28 |
| | Solution[2] | $1.25 \times 10^8$ | 0.26 |

[1]Placed blueberry, sliced strawberry, sliced green bean, sliced and cooked sweet potato into containers with 5051 powder as described above. *Pediococcus* coated blueberry, strawberry, green bean and sweet potato were placed on separate trays covered with parchment paper and freeze-dried.
[2]Transferred pieces of blueberry, sliced strawberry, sliced green bean, sliced and cooked sweet potato into 5051 solution as described hereinabove. *Pediococcus* coated blueberry, sliced strawberry, sliced green bean, sliced and cooked sweet potato were placed on separate trays covered with parchment paper and freeze-dried.

EXAMPLE 6

Use of Probiotic Fermentation Culture to Coat Foodstuffs

An additional experiment was conducted in order to determine whether fermentation cultures stored at room temperature for varying amounts of time could serve as a source of probiotic coatings instead of 5051 solution or 5051powder. Results are summarized in table 6.

Preparing probiotic bacteria directly from cultures and applying to foodstuffs before freeze-drying can increase efficiency and/or reduce cost of preparing probiotic coated freeze-dried products.

In order to examine this possibility, *P. acidilactici* NRRL B-50517 fresh cultures were prepared in fermenters, harvested probiotics, and resuspended in a cryoprotectant solution. These probiotic solutions were applied to sliced Gala apple and sliced Fuji apples then freeze-dried. We successfully detect the live probiotic from these probiotic Fuji apples and gala apples.

Results summarized in table 6 show the viability of *P. acidilactici* NRRL B-50517 was not appreciably decreased even after 64 days stored at room temperature. This demonstrates that fresh prepared *Pediococcus* probiotics can be applied to the materials for preparation of probiotic freeze-dried products, and these probiotic freeze-dried products are stable at room temperature storage.

TABLE 6

Detection of live probiotics from *Pediococcus* freeze-dried apples using *Pediococcus* prepared fresh by fermented cultures after stored at room temperature*

| Days stored at room temperature | Numbers of *P. acidilactici* NRRL B-50517 (CFU/g)** from probiotic freeze-dried Gala apples | Numbers of *P. acidilactici* NRRL B-50517 (CFU/g)** from probiotic freeze-dried Fuji apples |
|---|---|---|
| 1 | $2.00 \times 10^8$ | $2.50 \times 10^8$ |
| 8 | $2.90 \times 10^8$ | $3.35 \times 10^8$ |
| 24 | $1.30 \times 10^8$ | $1.10 \times 10^8$ |
| 40 | $1.78 \times 10^8$ | $1.33 \times 10^8$ |

TABLE 6-continued

Detection of live probiotics from Pediococcus freeze-dried apples using Pediococcus prepared fresh by fermented cultures after stored at room temperature*

| Days stored at room temperature | Numbers of P. acidilactici NRRL B-50517 (CFU/g)** from probiotic freeze-dried Gala apples | Numbers of P. acidilactici NRRL B-50517 (CFU/g)** from probiotic freeze-dried Fuji apples |
|---|---|---|
| 50 | $2.00 \times 10^8$ | $5.50 \times 10^8$ |
| 64 | $1.68 \times 10^8$ | $1.70 \times 10^8$ |

*Cut apples into ¼ inch slices, then cut those into halves. Transferred apple slices into the fresh prepared Pediococcus acidilactici NRRL B-50517 harvested from fermenters. Preparation of P. acidilactici NRRL B-50517 cultures harvested from fermenter-transferred 10 well separated to 10 ml MRS broth in 50 ml falcon tube and incubated at 45° C. overnight, transferred the 10 ml overnight bacterial cultures to 2 liters of fermenters and incubated at 100 rpm, 45° C. overnight, harvested the overnight bacterial cultures by centrifugation, added 150 ml solution of 7% sucrose, 7.5% lecithin to resuspend the bacterial cultures homogenously. After mixed the sliced apples with Pediococcus fermented cultures solution, placed the apple slices on the tray evenly, proceed the freeze-dried process until it completed.
**Measured 0.2 g to 0.4 g of Pediococcus probiotic freeze-dried apples stored at room temperature at desirable time, transferred the slice apple into 5 ml saline solution, and mixed well. Performed series of dilution, and plated 100 ul of desirable diluted solution onto MRS plates and incubated at the incubator overnight to count the colonies.

EXAMPLE 7

Coating with Yogurt

The most common application of probiotics is preparation of yogurt from milks. P. acidilactici NRRL B-50517 monoculture can be used to make yogurt. Unlike conventional yogurt starter cultures—Streptococcus thermophilus and Lactobacillus delbrueckii subsp. bulgaricus that die after yogurt formation, P. acidilactici NRRL B-50517 maintains viability after yogurt formation months in the refrigerator. This suggested yogurt can be a source of Pediococcus probiotics to apply to the foodstuffs before freeze-drying. In order to test this hypothesis, yogurt was prepared using P. acidilactici NRRL B-50517 and applied directly onto sliced apples followed by freeze-drying to prepare Pediococcus probiotic freeze-dried apples.

Results presented in table 7 show live P. acidilactici NRRL B-50517 from Pediococcus yogurt treated freeze-dried apples. These results suggest an alternative method to introduce Pediococcus probiotics onto freeze-dried foodstuffs and/or provide a way to introduce dairy products onto other foodstuffs.

TABLE 7

Detection of live probiotics from Pediococcus freeze-dried apples mixed with yogurt prepared by P. acidilactici NRRL B-50517*

| Freeze-dried apples mixed with yogurt Prepared from P. acidilactici NRRL B-50517 | Numbers of P. acidilactici NRRL B-50517 (CFU/g) from freeze-dried Gala apples mixed with Pediococcus made yogurt** |
|---|---|
| Sample 1 | $2.58 \times 10^7$ |
| Sample 2 | $4.15 \times 10^7$ |

*Cut apples into ¼ slices, then cut those into halves. Transferred apple slices into the yogurt prepared by P. acidilactici NRRL B-50517, mixed the apple slice with Pediococcus yogurt homogenously, transferred Pediococcus yogurt coated apple on the freeze-drying trays covered with parchment paper and freeze-dried.
Preparation Pediococcus yogurt:
**Measured 0.2 g to 0.4 g of Pediococcus probiotic freeze-dried apples, transferred the slice apple into 5 ml saline solution, and mixed well. Performed series of dilution, and plated 100 ul of desirable diluted solution onto MRS plates and incubated at the incubator overnight to count the colonies.

EXAMPLE 8

Freeze-Dried Substrate, Coated and Freeze-Dried Again

In order to examine the possibility of coating a freeze-dried substrate with solution 5051 the freeze-drying again, an experiment was conducted using apples. Results summarized in table 8 indicate a 100-fold decrease in viable bacteria as a result of freeze-drying.

TABLE 8

Detection of live probiotics from Pediococcus freeze-dried apples by applying probiotics solution onto freeze-dried apples with P. acidilactici NRRL B-50517* and through the 2nd freeze-dried process.

| Amounts of P. acidilactici NRRL B-50517 solution spraying onto freeze-dried apples | Numbers of P. acidilactici NRRL B-50517 (CFU/g) from multiple freeze-dried Gala apples mixed with P. acidilactici NRRL B-50517 |
|---|---|
| 1 × 109 CFU probiotic onto per g freeze-dried apple | $2.30 \times 10^7$ |
| 2 × 109 CFU probiotic onto per g freeze-dried apple | $4.50 \times 10^7$ |

*Cut apples into ¼ inch slices, then cut those into halves. Transferred apple slices on the freeze-drying trays covered with parchment paper, freeze-dried, removed the tray, and sprayed Pediococcus probiotic solution 5051 onto freeze-dried apples and freeze-dried again.
**Measured 0.2 g to 0.4 g of Pediococcus probiotic freeze-dried apples, transferred the slice apple into 5 ml saline solution, and mixed well. Performed series of dilution, and plated 100 ul of desirable diluted solution onto MRS plates and incubated at the incubator overnight, then counted the colonies.

EXAMPLE 9

HEAT Treatment of Probiotic Freeze-Dried Meat Products

P. acidilactici NRRL B-50517 is shown to be able to survive after high temperature (up to 85° C.), high osmotic stress (example 11 hereinbelow), and low pH treatment (example 10 hereinbelow). It is also more tolerant to the antibiotics treatment (Example 12 hereinbelow).

A series of experiments was conducted In order to determine whether P. acidilactici NRRL B-50517 maintains desired qualities after freeze-drying.

After incubating both Pediococcus freeze-dried beef meat and Pediococcus probiotic freeze-dried chicken livers at 65° C. incubator for 30 min, live P. acidilactici NRRL B-50517 is detected from both Pediococcus probiotic beef meat and Pediococcus probiotic chicken livers. Further after treatment these Pediococcus probiotics at 85° C. for 10 min and 30 min after incubated at 65° C. for 30 minutes, we were able to detect 20% to 30% survival of P. acidilactici NRRL B-50517 compared to those stored at room temperature only (Table 9). Results summarized in table 9 indicate that P. acidilactici NRRL B-50517 not only survive through the freeze-dried process but also maintains the unique characteristics of high temperature resistance

TABLE 9

Survival of Probiotics after elevated temperature treatment of Pediococcus probiotic freeze-dried beef meat and chicken livers

| | Treatment* | Number of P. acidilactici NNRL B-50517 (CFU/g) ** | % survival |
|---|---|---|---|
| Beef meat | Room temperature | $2.24 \times 10^8$ | 100% |
| | 65° C., 30 min | $8.75 \times 10^7$ | 39.11% |
| | 65° C., 30 min followed by 85° C., 10 min | $4.75 \times 10^7$ | 21.23% |

TABLE 9-continued

Survival of Probiotics after elevated temperature treatment of *Pediococcus* probiotic freeze-dried beef meat and chicken livers

|  | Treatment* | Number of P. acidilactici NNRL B-50517 (CFU/g) ** | % survival |
|---|---|---|---|
| Chicken livers | 65° C., 30 min followed by 85° C., 30 min | $5.13 \times 10^7$ | 22.91% |
|  | Room temperature | $1.18 \times 10^8$ | 100% |
|  | 65° C., 30 min | $4.00 \times 10^7$ | 34.04% |
|  | 65° C., 30 min followed by 85° C., 10 min | $4.25 \times 10^7$ | 36.17% |
|  | 65° C., 30 min followed by 85° C., 30 min | $7.50 \times 10^7$ | 63.83% |

*Incubated *Pediococcus* probiotic freeze-dried beef meat or *Pediococcus* probiotic freeze-dried chicken livers at elevated temperature –65° C. for 30 minutes, 65° C. for 30-minute following by 85° C. for another 10 minutes or by 85° C. for another 30 minutes, then measured the detection of probiotics as described at Table 7. Control was to take the *Pediococcus* freeze-dried beef meat or the *Pediococcus* freeze-dried chicken livers at room temperature without being treated at elevated temperature and performed the probiotic assays directly.

EXAMPLE 10

Low pH Treatment

In order to demonstrate that probiotic freeze-dried products can survive at the stomach acid, 5051 probiotic freeze-dried apples were placed into water adjusted to pH 7.0, 5.0, 3.0 and 2.0, and incubated at room temperature from 30 minutes to 3 hours. Results summarized in table 10 show there are no detectable viable bacteria when 5051 freeze-dried apples were incubated at pH 3.0 up to 1 and ½ hours. However, there is about 1.0% survival of probiotics when incubated at the pH 2.0 for 30 minutes but no further decrease was detectable up to 3-hour incubation at pH 2.0, room temperature (example 10). These results showed *Pediococcus acidilactici* NRRL B-50517 can integrated into the food through freeze-dried process, and still maintain the resistance to the acidic environment of the stomach.

apples were incubated in water with concentrations of sodium chloride varying from 0.1% (saline), 1.0%, 5.0%, 10.0% and 20.0% for 30 minutes, 1 hour, 2 hours and overnight at room temperature. Results summarized in table 11 show no detectable viability difference in *P. acidilactici* NRRL B-50517 from 0.1% to 20% NaCl solution up to 2-hour incubation at room temperature. Even after overnight incubation at the 20% NaCl solution, more than 22% survival is observed. Therefore, the *P. acidilactici* NRRL B-50517 freeze-dried products maintain the high resistance of *Pediococcus* probiotics to the high salt treatment.

TABLE 11

Detection of live probiotics from *Pediococcus* freeze-dried apples treated with different concentration of salts*

| Concentration of NaCl | 30 minutes | 1 hour | 2 hours | Overnight |
|---|---|---|---|---|
| 0.1% | $9.15 \times 10^7$ | $1.03 \times 10^7$ | $7.63 \times 10^6$ | $3.13 \times 01^6$ |
| 1.0% | $3.63 \times 10^6$ | $1.83 \times 10^7$ | $1.73 \times 10^7$ | $3.73 \times 10^6$ |
| 5.0% | $3.20 \times 10^6$ | $1.81 \times 10^7$ | $1.33 \times 10^7$ | $3.05 \times 10^6$ |
| 10.0% | $1.09 \times 10^7$ | $9.13 \times 10^6$ | $6.13 \times 10^6$ | $4.88 \times 10^5$ |
| 20.0% | $3.25 \times 10^6$ | $9.28 \times 10^6$ | $5.38 \times 10^6$ | $7.13 \times 10^5$ |

*Measured 0.2 g to 0.4 g of *Pediococcus* probiotic freeze-dried apples, transferred the sliced apple into 5 ml different salt solutions (0.1%, 1.0%, 5.0%, 10.0%, and 20.0%) adjusted, mixed well, incubated at room temperature for thirty minutes, one and half hours and three hours. After incubation, transferred 100 µl solution from the falcon tube, performed series of dilution, and plated 100 µl of desirable diluted solution onto MRS plates and incubated at the incubator overnight to count the colonies. Numbers were the average of two repeated experiments.

EXAMPLE 12

Antibiotic Compatibility

Antibiotics are often prescribed to prevent and treat the infectious diseases. Adverse side effects of antibiotics are often reported, especially for those required to take the antibiotics for a long period. Probiotics are reported to decrease the side effects of antibiotics, especially related to digestive disorders. *Pediococcus acidilactici* is more toler-

TABLE 10

Detection of live probiotics from *Pediococcus* freeze-dried apples treated after acidic treatment*

| Sterilized water with different pH | 30 min | | 1½ hrs | | 3 hrs. | |
|---|---|---|---|---|---|---|
| | Number of P. acidilactici NNRL B-50517 (CFU/g)** | % of survival | Number of P. acidilactici NNRL B-50517 (CFU/g)** | % of survival | Number of P. acidilactici NNRL B-50517 (CFU/g)** | % of survival |
| pH 7.0 | $5.50 \times 10^7$ | 100.00% | $4.35 \times 10^7$ | 100.00% | $6.0 \times 10^7$ | 100% |
| pH 5.0 | $3.38 \times 10^7$ | 61.36% | $3.63 \times 10^7$ | 85.29% | $5.25 \times 10^7$ | 87.50% |
| pH 3.0 | $6.25 \times 10^7$ | 113.64% | $6.75 \times 10^7$ | 158.82% | $2.38 \times 10^7$ | 39.58% |
| pH 2.0 | $6.25 \times 10^5$ | 1.14% | $2.50 \times 10^5$ | 0.59% | $1.49 \times 10^5$ | 1.46% |

*Measured 0.2 g to 0.4 g of Pediococcus probiotic freeze-dried apples, transferred the slice apple into 5 ml sterilized water adjusted with HCl to the desirable pH in a 15 ml falcon tube, mixed well, incubated at room temperature for thirty minutes, one and half hours and three hours. After incubation, transferred 100 µl solution from the falcon tube, performed series of dilution, and plated 100 ul of desirable diluted solution onto MRS plates and incubated at the incubator overnight to count the colonies. Numbers were the average of two repeated experiments

EXAMPLE 11

Osmotic Stress

The mammalian digestive system contains bile salts and stomach acids that can interfere with the ability of probiotic bacteria to reach relevant portions of the GI tract to exert beneficial effects. In order to learn if 5051 freeze-dried products can resist high salt treatment, 5051 freeze-dried ant to the antibiotics killing effects and is recommended as an adjunct to antibiotics treatment.

In order to determine whether freeze-drying interfered with this antibiotic compatibility, *Pediococcus* probiotic freeze-dried products were exposed amoxicillin at 10 µg/ml, 50 µg/ml, 100 µg/ml, and 500 µg/ml, and incubated at 45° C. for fours to see if any survival of *Pediococcus acidilactici* NRRL B-50517. Results summarized in table 12 indicate all of antibiotics treatment showed greater than 700 million live *Pediococcus acidilactici* NNRL B-50517 in one ml of MRS broth even at the high concentration of 500 μg/ml of amoxicillin treatment. This result suggests that *Pediococcus* freeze-dried products can be applied together with antibiotics treatment as a substitute for *Pediococcus acidilactici* NRRL B-50517 fermentation powder products. For comparison, *E. coli* had 0% survival at 500 μg/ml of amoxicillin (data not shown).

TABLE 12

Detection of live probiotics from *Pediococcus* freeze-dried apples treated with antibiotics for 4 hours*

| Concentration of Amoxicillin (μg/ml) | Number of *P. acidilactici* NRRL B-50517 (CFU/ml) |
|---|---|
| 0 | $1.78 \times 10^9$ |
| 10 | $7.38 \times 10^7$ |
| 50 | $9.25 \times 10^7$ |
| 100 | $7.13 \times 10^7$ |
| 500 | $1.01 \times 10^8$ |

*Measured 0.2 g to 0.4 g of *Pediococcus* probiotic freeze-dried apples, transferred the slice apple into 5 ml MRS broth with 0 μg/ml, 10 μg/ml, 50 μg/ml, 100 μg/ml and 500 μg/ml amoxicillin, incubated at 45 C. for 4 hours, and performed the detection of viability of *P. acidilactici* NRRL B-50517. After incubation, transferred 100 μl solution from the falcon tube, performed series of dilution, and plated 100 μl of desirable diluted solution onto MRS plates and incubated at the incubator overnight to count the colonies. Numbers were the average of two repeated experiments.

After exposure probiotic freeze-dried products to elevated temperature, low pH, high salts, and antibiotics, reasonable amounts of live probiotics can still be detected from treated probiotic freeze-dried probiotics. These results indicate that probiotic freeze-dried products can be the alternative delivery of probiotics to humans and animals.

EXAMPLE 13

Freeze-Dried Apples

In order to determine the amenability of various commercial strains of apples to serve as a substrate for delivery of freeze-dried bacteria a comparison was conducted. Results summarized in table 13 indicate that there is no significant difference between Red delicious, Fuji and Gala apples.

TABLE 13

Detection of live probiotics from *Pediococcus* probiotics freeze-dried apples*

| Variety of Apple | Numbers of *P. acidilactici* NRRL B-50517 (CFU/g)** |
|---|---|
| Red Delicious | $5.5 \times 10^8$ |
| Fuji | $2.28 \times 10^8$ |
| Gala | $2.18 \times 10^8$ |

*Cut apples into 1/4 slices, then cut those into halves. Transferred apple slices into the *Pediococcus acidilactici* NRRL B-50517 solution [mixed 20 g of *Pediococcus* fermentative probiotics for freeze-dried powders (catalogue number PA-5051FD, Imagilin Technology, LLC) with 80 ml water], mixed the sliced apples and probiotic solution for 45 secs to a min, transferred *Pediococcus* coated apple on the freeze-drying trays covered with parchment paper and freeze-dried.
**Measured 0.2 g to 0.4 g of *Pediococcus* probiotic freeze-dried apples, transferred the slice apple into 5 ml saline solution, and mixed well. Performed series of dilution, and plated 100 ul of desirable diluted solution onto MRS plates and incubated at the incubator overnight to count the colonies.

EXAMPLE 14

Freeze-Dried Apples and Heat Treatment

In order to determine the effect of elevated temperature on probiotic bacteria freeze-dried onto foodstuffs, an experiment with different temperature conditions was conducted. Results, summarized in table 14 indicate that *P. acidilactici* NNRL B-50517 exhibited about 73% survival after 30 minutes at 65° C. and 30 minutes at 85° C.

TABLE 14

Survival of Probiotics after elevated temperature treatment of *Pediococcus* probiotic freeze-dried apples

| Treatment* | Number of *P. acidilactici* NNRL B-50517 (CFU/g) | % survival |
|---|---|---|
| Room temperature | $2.41 \times 10^8$ | 100% |
| 65° C., 30 min | $2.32 \times 10^8$ | 96.22% |
| 65° C., 30 min followed by 85° C., 10 min | $2.35 \times 10^8$ | 97.39% |
| 65° C., 30 min followed by 85° C., 30 min | $1.76 \times 10^8$ | 72.92% |

*Incubated *Pediococcus* probiotic freeze-dried apples at elevated temperature –65° C. for 30 minutes, 65° C. for 30-minute following by 85° C. for another 10 minutes or by 85° C. for another 30 minutes, then performed the detection of probiotics as described at Table 1. Control was to take the sliced *Pediococcus* freeze-dried apples at room temperature without being treated at elevated temperature and performed the probiotic assays directly.

EXAMPLE 15

Freeze-Dried Sweet Potato and Heat Treatment

In order to confirm the results of example 14, an additional experiment was conducted using sweet potato as a substrate. Results, summarized in table 15 indicate that *P. acidilactici* NNRL B-50517 exhibited about 61% survival after 30 minutes at 65° C. and 30 minutes at 85° C.

TABLE 15

Survival of Probiotics after elevated temperature treatment of *Pediococcus* probiotic freeze-dried sweet potato

| Treatment* | Number of *P. acidilactici* NNRL B-50517 (CFU/g) | % survival |
|---|---|---|
| Room temperature | $4.32 \times 10^8$ | 100% |
| 65° C., 30 min | $5.71 \times 10^8$ | 132.40% |
| 65° C., 30 min followed by 85° C., 10 min | $3.60 \times 10^8$ | 83.41% |
| 65° C., 30 min followed by 85° C., 30 min | $2.64 \times 10^8$ | 61.10% |

*Incubated *Pediococcus* probiotic freeze-dried sweet potato at elevated temperature –65° C. for 30 minutes, 65° C. for 30-minute following by 85° C. for another 10 minutes or by 85° C. for another 30 minutes, then performed the detection of probiotics as described at Table 1. Control was to take the sliced *Pediococcus* freeze-dried apples at room temperature without being treated at elevated temperature and performed the probiotic assays directly.

EXAMPLE 16

Freeze-Dried Apples Stored at 40° C.

In order to determine the effect of a 40° C. storage temperature on probiotic bacteria freeze-dried onto foodstuffs, an experiment was conducted using apples as a substrate. Results, summarized in table 16 suggest that *P. acidilactici* NNRL B-50517 is not adversely effected by exposure to 40° C. for up to 12 days.

TABLE 16

Detection of viable probiotics from *Pediococcus* probiotic freeze-dried probiotic apples stored at 40° C.

| Incubation Time for (days) at 40° C.* | Numbers of *Pediococcus acidilactici* NRRL B-50517 | % of survival |
|---|---|---|
| control | $3.25 \times 10^8$ | 100% |
| 4 | $1.63 \times 10^8$ | 81% |

TABLE 16-continued

Detection of viable probiotics from *Pediococcus* probiotic freeze-dried probiotic apples stored at 40° C.

| Incubation Time for (days) at 40° C.* | Numbers of *Pediococcus* acidilactici NRRL B-50517 | % of survival |
|---|---|---|
| 7 | $5.00 \times 10^8$ | 153% |
| 12 | $4.14 \times 10^8$ | 127% |

*Incubated *Pediococcus* probiotic freeze-dried apples at the elevated temperature 40° C. incubator. After 4 days, 7 days, and 12 days incubation, removed the elevated temperature treated *Pediococcus* probiotic freeze-dried apple, performed the detection of probiotics assays as described at Table 1. Control was to take the sliced *Pediococcus* freeze-dried apples at room temperature without being treated at elevated temperature and performed the probiotic assays directly.

EXAMPLE 17

Freeze-Dried Apples Stored at 65° C.

In order to determine the effect of a 65° C. storage temperature on probiotic bacteria freeze-dried onto foodstuffs, an experiment was conducted using apples as a substrate. Results, summarized in table 17 suggest 1% to 2% of *P. acidilactici* NNRL B-50517 survive after 7 to 12 days.

TABLE 17

Detection of viable probiotics from *Pediococcus* probiotic freeze-dried probiotic apples stored at 65° C.

| Incubation Time for (days) at 65° C.* | Numbers of *Pediococcus* acidilactici NRRL B-50517 | % of survival |
|---|---|---|
| control | $3.25 \times 10^8$ | 100% |
| 4 | $2.65 \times 10^6$ | 0.81% |
| 7 | $6.38 \times 10^6$ | 1.96% |
| 12 | $3.88 \times 10^6$ | 1.19% |

*Incubated *Pediococcus* probiotic freeze-dried apples at the elevated temperature 65° C. incubator. After 4 days, 7 days, and 12 days incubation, removed the elevated temperature treated *Pediococcus* probiotic freeze-dried apple, performed the detection of probiotics assays as described at Table 1. Control was to take the sliced *Pediococcus* freeze-dried apples at room temperature without being treated at elevated temperature and performed the probiotic assays directly.

EXAMPLE 18

Viability of Bacteria on Various Substrates

In order to determine the amenability of various types of fruit and vegetables to serve as a substrate for delivery of freeze-dried bacteria a comparison was conducted. Results summarized in table 18 indicate that blueberry, strawberry, green bean and sweet potato are all suitable substrates for delivery of freeze-dried probiotic bacteria.

TABLE 18

Detection of live probiotics from *Pediococcus* freeze-dried food

| Type of Fruit or Vegetable | Numbers of *P. acidilactici* NRRL B-50517 (CFU/g)* |
|---|---|
| Blueberry | $7.33 \times 10^7$ |
| Green Beans | $1.61 \times 10^8$ |
| Strawberry | $1.93 \times 10^8$ |
| Sweet Potato | $3.00 \times 10^8$ |

*Measured 0.2 g to 0.4 g of *Pediococcus* probiotic freeze-dried blueberry, green berry, strawberry, or sweet potato, transferred the slice apple into 5 ml saline solution, and mixed well. Performed series of dilution, and plated 100 ul of desirable diluted solution onto MRS plates and incubated at the incubator overnight to count the colonies.

It should be understood that the claims provided herewith are not an exhaustive representation of the invention, but that further claims may be added.

The invention claimed is:

1. A composition, comprising:
 (a) pieces of freeze-dried foodstuff and (b) a coating layer consisting essentially of viable freeze-dried probiotic bacteria applied to said freeze-dried foodstuff and adhering to said pieces; wherein the probiotic bacteria are *Pediococcus acidilactici* NRRL B-50517.

2. The composition according to claim 1, wherein said foodstuff is at least one item selected from the group consisting of fruits, vegetables, meats, nuts and dairy products.

3. The composition of claim 1 wherein the composition comprises a preservative.

4. The composition of claim 1, wherein the composition comprises an antioxidant.

5. The composition of claim 1, said coating layer containing at least $1 \times 10^5$ CFU of probiotic bacteria per gram of composition.

6. A product produced by a process comprising (1) providing a solution or powder composition consisting essentially of viable freeze-dried probiotic bacteria; (2) mixing or coating at least one food selected from the group consisting of fruit, vegetable, meat, and nuts, with the freeze-dried probiotic bacteria solution or powder composition, and (3) without further processing, freeze-drying the at least one mixed or coated food to make the product, wherein the product comprises viable probiotic bacteria, wherein the probiotic bacteria are *Pediococcus acidilactici* NRRL B-50517.

7. The product of claim 6, wherein the at least one food of part (2) is fruit, vegetable or nuts, wherein the fruit, vegetable or nuts have been exposed to the probiotic bacteria and freeze dried prior to mixing or coating with the composition consisting essentially of the viable freeze-dried probiotic bacteria of part (1).

8. The product of claim 6, wherein the at least one food of part (2) is meat, wherein the meat has been either cooked or subjected to a salting process to destroy harmful organisms.

* * * * *